United States Patent [19]

Snyder

[11] 4,379,863
[45] Apr. 12, 1983

[54] COPOLYMER COMPOSITION AND DELIVERY SYSTEM FOR PROVIDING A PROTECTIVE BARRIER FILM FOR THE SKIN

[75] Inventor: Martin Snyder, North Plainfield, N.J.

[73] Assignee: C. R. Bard, Inc., Murray Hill, N.J.

[21] Appl. No.: 224,700

[22] Filed: Jan. 13, 1981

[51] Int. Cl.³ .............................................. C08J 7/02
[52] U.S. Cl. .................................. 523/105; 524/391; 524/296
[58] Field of Search .................. 524/296, 46, 391; 523/105, 111

[56] References Cited

U.S. PATENT DOCUMENTS 3,175,989  3/1965  Cannon et al. ...................... 524/296
3,987,000  10/1976  Gleichenhogan et al. .......... 526/324

Primary Examiner—Joseph L. Schofer
Assistant Examiner—N. Sarofim
Attorney, Agent, or Firm—Dennison, Meserole, Pollack & Scheiner

[57] ABSTRACT

A copolymer-based film former composition and delivery system is disclosed for establishing a breathable, compliant, water-insoluble barrier film for protection of the skin from exposure to, and irritation by, urine or fecal waste. The film formed establishes a protective barrier film that aids in maintaining a normal skin environment such as at the site of an interface between the skin and the adhesive of an ostomy appliance. In a preferred embodiment the copolymer comprises a plasticized solution of 50/50 n-butyl/iso-butyl methacrylate. The film former is applied to the skin by delivery means adapted to essentially preclude cross-contamination, assure that the film intimately conforms to the skin, and in a preferred delivery system enables the essentially simultaneous removal of a previously deposited film with stomal contaminant thereon while establishing a new film formed of the copolymer composition.

19 Claims, No Drawings

COPOLYMER COMPOSITION AND DELIVERY SYSTEM FOR PROVIDING A PROTECTIVE BARRIER FILM FOR THE SKIN

BACKGROUND OF THE INVENTION

This invention relates to an improved film-forming composition for providing a barrier film on the skin to protect the skin from irritation by body fluids and adhesively secured appliances as encountered by ostomates.

As is very often the case with the use of an ostomy appliance, a significant problem exists with respect to avoiding skin irritation. The important concept in skin breakdown is that the natural barrier properties of the skin have been breached and the body is now vulnerable.

With an ostomy, the continuous application and removal of aggressive adhesively secured appliances creates a maceration of the outer protective layer of the skin. When this layer is stripped away, the inner, i.e., living, layer containing the glands, blood vessels, nerves and muscle fiber is particularly vulnerable to the corrosive effects of feces and urine, and severe skin damage can occur.

In the case of the ileostomate, continuous application and removal of adhesively secured appliances as well as the acidity, the enzymatic activity and bacteria of the stomal discharge can create havoc around the stoma.

More common to all ostomates are the monilial infections that occur in the moist, dark environments found under appliances.

A frequent recommendation in this condition is the use of a skin barrier at the interface between the skin and appliance adhesive. However, many of the prior barriers suggested exacerbate the very problems they are intended to alleviate. For example, most preformed wafer barrier devices are occlusive since moisture vapor coming off the skin cannot pass through them. Moisture is thus trapped to a greater or lesser extent, depending upon the type of barrier used. Also, light cannot pass through such barriers, creating a dark as well as a moist environment that is ideal for further yeast growth.

The ostomate is not the only one whose skin comes under attack from adverse conditions. Permanently or temporarily disabled persons find themselves confronted by similar situations. Any time one is subjected to immobility, compounded by incontinence of bladder or bowel, skin-threatening conditions can occur. In all cases one common denominator exists. The natural barrier protection offered by the skin has been compromised.

Attempts have been made in the past to provide a skin coating material in the form of a liquid which may be applied to the skin by a sponge or other means. Because the liquid is extremely fluid, it was difficult to maintain the liquid in place until it had dried, and often the user was required to lie on their back while applying the liquid and permitting the same to dry to form a protective coating. This provided a far from satisfactory means for attempting to establish a skin coating.

It is recognized as described in U.S. Pat. No. 3,269,903 that a significant problem with liquid plastic dressings is a lack of adequate diffusion of vapor after the solvent evaporates leaving a film. The patent is directed to attempting to solve this major problem that is attributed to the inclusion of plasticizers in the liquid dressing compositions. The patent is thus principally directed to the provision of plasticizer-free liquid plastic dressings such as consisting of solutions of polymeric-2-methoxyethylmethacrylate or polymeric-2-ethoxyethyl-methacrylate for forming a vapor permeable skin coating. In comparing the vapor permeability of the coatings of the invention with coatings formed of other polymers, the permeability of films of polybutyl methacrylate per se and polyisobutyl methacrylate per se were investigated and found to be meager and thus presumably not suitable for the intended utility. However, problems that may be encountered with the polymeric-2-ethoxyethyl methacrylate film of this patent are briefly discussed in U.S. Pat. No. 3,987,000, see column 3.

Other attempts as exemplified by U.S. Pat. No. 3,876,771, have provided a skin coating or skin protective material in the form of a gel. The gel is sufficiently stiff as to be able to support itself in position without running, even when applied to the skin surface surrounding the stoma while the person is standing. While the gel is capable, under favorable conditions, of drying to a thin protective coating against which the adhesive or other sealing means of the ostomy appliance may be pressed, the film formed on the skin is generally relatively soluble in water, especially soapy water. Thus, stomal fluid discharges and particularly ileal conduit discharges, which are primarily water, adversely effect the integrity of the barrier formed.

With further reference to U.S. Pat. No. 3,987,000, it will be seen that it is known, particularly in connection with compositions that can be sprayed from aerosol containers, that a mixed polymeride derived by mixed polymerization of isobutene with lower acrylic or methacrylic acid esters and maleic acid monoesters, and wherein the patent is primarily directed to providing a non-blocking film by the addition of the maleic acid monoesters to the monomer mixture prior to polymerization. However, as stated in this patent, see column 6, such films, according to the invention, resist short stresses when washing with soap and water. It is thus acknowledged that the copolymers proposed are not in the accepted sense water-insoluble. This patent is particularly noteworthy with respect to the myriad of requirements for polymer systems having utility as film formers for application to the skin. The copolymer systems proposed therein appear to be capable of satisfying numerous of the requirements, but it is to be noted that such copolymer systems still do not satisfy the significant requirement of providing an essentially water-insoluble film.

From the lengthy discussion in U.S. Pat. No. 3,987,000 with respect to the desired advantageous characteristics of film-forming polymer compositions for application to the skin, it is believed that it will readily be apparent that far more than routine experimentation is required in order to provide a suitable skin protective barrier, or film, based upon known film-forming polymers or copolymers.

In this latter regard, it is recognized that solutions of the n-butyl and isobutyl esters of methacrylic acid, and copolymers thereof, have utility as film formers per se, as will be appreciated from U.S. Pat. No. 2,129,668.

U.S. Pat. No. 2,804,073 is directed to a resinous film-former for application to the skin and wherein there is broadly disclosed the utilization of polymethacrylic ester polymers and compatible combinations thereof. However, insofar as polymethacrylic ester polymers are concerned, the specific Examples, see Example 2, only show the utilization of n-butyl methacrylate polymer.

However, the myriad of interrelated properties essential to the formation and maintenance of a protective barrier film on the skin, particularly for ostomates, presents a highly complex problem that requires far more than routine experimentation in addition to the knowledge that particular polymers, copolymers, etc. have known utility as film formers.

BRIEF SUMMARY OF THE INVENTION

In accordance with the invention there is provided a film-forming composition for establishing a protective barrier film on the skin while satisfying the following objectives.

The barrier film established should protect the skin from attack by acids, caustics and active enzymes found in human waste by providing a waterproof barrier that normally encountered liquids could not penetrate or wash away.

The film established should form a breathable surface barrier over the skin that is permeable to oxygen, water vapor and carbon dioxide while not encouraging the growth of micro-organisms.

The barrier film formed should provide an interface between the skin and an aggressive adhesive, which film lifts off with the adhesive, thus also protecting the skin from adhesive maceration.

The barrier film formed should faithfully conform to the contours of the skin.

The barrier film formed should be readily removable from the skin together with body fluid contaminant thereon, preferably with simultaneous deposition of a non-contaminated barrier film.

DETAILED DESCRIPTION OF THE INVENTION

These and other objectives are satisfied by the provision of a film forming composition comprising a copolymer derived from straight chan lower esters of methacrylic acid, principally $C_1$-$C_4$, dissolved in a volatile physiologically acceptable organic solvent and further including a minor amount of compatible physiologically acceptable platicizer. A preferred copolymer comprises a 50/50 copolymer of n-butyl/isobutyl methacrylate such as commercially available from Du Pont and distributed under the registered trademark of Elvacite, and specifically Elvacite 2046. Other suitable copolymers comprise AKRALOID-B66 and AKRALOID-B67 available from Rohm and Haas which are primarily Iso-butyl methacralates. The copolymers may of course be derived by reaction of the appropriate monomers by processes well known in the art. Extensive technical data with respect to the preferred copolymer may be found in the Du Pont publication "Elvacite Acrylic Resins", December 1978 available from Du Pont Company, Plastic Products and Resins Department, Commercial Resins Division, Wilmington, Del. 19898. In this regard Elvacite 2046 is a high molecular weight, e.g., MW over 200,000, medium-hardness n-butyl/isobutyl methacrylate 50/50 copolymer having an inherent viscosity of 0.54, i.e., a solution containing 0.25 g copolymer in 50 ml methylene chloride, measured at 20° C. using a Cannon-Fenske viscometer.

The preferred copolymer is soluble in the higher, i.e., $C_3$-$C_{10}$ Aliphatic alcohols, and it has been found that isopropanol, IPA, is a highly suitable solvent particularly in view of the fact that it has a high degree of physiological acceptability. The preferred solvent comprises isopropanol diluted with water to 95% IPA. An alternative solvent comprises IPA diluted with water to a minimum of 85% IPA. Such butyl methacrylate resins are also readily soluble in VM&P naphtha and some grades of mineral spirits. While the butyl methacrylate resins are soluble in higher aliphatic alcohols including cyclohexanol, and in benzyl and furfuryl alcohols, as well as alcohols with an aromatic character, to name only a few solvents, it will be understood that a significant aspect of selection of a solvent resides in requirement that the solvent be physiologically acceptable when in prolonged contact with the skin.

Suitable solvents comprise 95% isopropanol, and 85% isopropanol, i.e., isopropanol diluted with water to the minimum percentage indicated.

Despite the fact that butyl methacrylate copolymers, such as Elvacite 2046, are not normally considered to require platicization, it has been found that a phthalate ester and particularly dimethyl phthalate (DMP) is highly suitable. While the preferred plasticizer is DMP such as distributed by Eastman Kodak under the registered trademark Kodaflex DMP, another operable, but not as satisfactory, plasticizer comprises ethyl cellulose.

A significant aspect of the invention resides in the relationship between the copolymer and solvent-plasticizer. In this regard, the ratio of copolymer to solvent-plasticizer is to a significant degree dependent upon the mans by which the composition is applied to the skin. The invention contemplates delivery of the system, that is, application of the copolymer composition to the skin by highly tailored systems, each having distinct advantages. The copolymer composition, in accordance with the invention, is preferably applied to the skin by aerosol, dabbing bottle, or wipe and wherein at least the wipe delivery system provides a means for removing a body fluid contaminated protective barrier layer while simultaneously depositing a new non-contaminated protective barrier film.

For purposes of this disclosure, it will be understood that all percentages expressed are in terms of percentage by weight.

To provide a protective barrier film that satisfies the objects of this invention, approximately 5.0% to approximately 12.5% copolymer is dissolved in sufficient solvent to q.s. 100% when taking into consideration the subsequent admixture of from about 2% to about 4% plasticizer with the polymer-solvent system. It has been found that about 3% plasticizer is preferred. The criticality of not exceeding the aforediscussed relationship of the maximum percentage by weight of copolymer to solvent-plasticizer is far more than just a mere matter of choice. To provide the requisite essential interrelated parameters of the plasticized copolymeric film formed requires a significant degree of experimentation. It will also be understood that, particularly as discussed hereinafter with respect to the wipe delivery system, it has been discovered that utilization of a rather narrow ratio range of solvent to copolymer enables solvating a previously deposited contaminated protective barrier film, such as contaminated with fecal matter, while substantially simultaneously depositing the film forming copolymer composition so as to form a new non-contaminated protective barrier film upon volatilization of the solvent.

With specific reference to the relationship of copolymer to solvent-plasticizer for delivery by aerosol means, such as comprising charging of a conventional aerosol container with the liquid copolymer film forming composition and appropriate propellant, such as isobutane, it has been discovered that from about 5.0% to about 12.5% copolymer to solvent-plasticizer provides a protective barrier film that satisfies the objectives of the invention. In a preferred aerosol delivery system, the copolymer film forming composition comprises about 11%±0.5% copolymer to solvent-plasticizer.

The aerosol delivery system is particularly suited for the provision of a protective barrier film on skin areas of uneven topography and comprises a delivery system that is suitable for institutional use as well as home use by virtue of the fact that there is little if any opportunity for cross-contamination. It will of course be appreciated that the film forming composition for all practical purposes comprises a biocidal composition with respect to the microorganisms normally encountered in the environment within which it is used.

A copolymer film forming composition in accordance with the invention is also highly suitable for application to the skin by means of a reservoir applicator having a felt applicator pad, or dabber, continuously moistened by the gravimetric flow of the composition within the container. The dabbing system of delivery of the copolymer film former composition is for the most part for direct consumer utilization, i.e., home care, since it will be appreciated that, despite the essentially bactericidal properties of the copolymer film former composition, there might possibly exist a chance of affecting cross-contamination in an institutional environment where a dabbing applicator might inadvertently be utilized by more than one person. It has been discovered that, to ensure the provision of a protective barrier film that meets the objectives of the invention, when using the dabbing applicator, the copolymer, e.g. 50/50 n-butyl/isobutyl methacrylate, should comprise no more than about 12%, i.e., 12%±0.5%, of the film former composition. This is particularly so when it is anticipated that during storage or shipment there is a possibility that the composition will be subjected to wide swings of temperature as might cause the polymer to salt-out at relatively low temperatures whereby redissolution of the copolymer would at best be difficult.

Turning now to the wipe delivery system, it will be understood that the term "wipe" refers to individually packaged portions of "toweling" impregnated with a copolymer film forming composition in accordance with the invention. It has somewhat unexpectedly been discovered that the utilization of a particular nonwoven fabric for the wipe delivery system enables the essentially simultaneous removal of a stomal fluid, or other fluid, contaminated protective barrier film with essentially simultaneous deposition of sufficient non-contaminated copolymer film former composition to form, upon evaporation of the solvent, a non-contaminated new protective barrier film. In this regard, an exemplary toweling comprises the nonwoven fabric referenced which is distributed by The Kendall Fiber Company, Products Division, Boston, Mass., under the registered trademark NOVONETTE. More particularly, grade No. 9812 comprising a rayonpolypropylene fiber content having a weight in the order of 74.1 grams per square yard and understood to be manufactured in accordance with the teachings of U.S. Pat. No. 3,542,634, Nov. 24, 1970 is preferred. The disclosure of U.S. Pat. No. 3,542,634 is hereby incorporated by reference so as to provide an enabling disclosure with respect to the production of towelette material, which which impregnated with the copolymer film forming composition of the present invention, provides a delivery system having the aforediscussed attributes. The towelette of U.S. Pat. No. 3,542,634 by virtue of fusion bonding of certain of the fibers at discrete locations, and having a "waffle" structure, is characterized by areas of differential absorbability and "hand", i.e., relative softness or harshness so as to provide a combined means for solvating and mechanically removing a previously deposited contaminated barrier film and simultaneously depositing a new non-contaminated barrier film.

It has further been discovered that the percentage of copolymer, e.g. 50/50 n-butyl/isobutyl methacrylate to solvent-plasticizer in a wipe delivery system is to be in the order of about 11%, i.e., 10.5% to 11.5%. Further, while it is not wished to be limited, it is theorized that the differential density, and thus differential absorption of the embossed nonwoven Kendall fabric is such that the relatively non-compressed areas of the towelette contain a high proportion of the copolymer film former composition impregnant whereby with the mildly abrasive property of said noncompressed portion of the towelette, the contaminated film is solvated and "mopped up" and the copolymer film former composition carried in the depressed, i.e., compressed fiber portions, of the towelette is deposited to establish a new non-contaminated protective barrier film.

EXAMPLES

The following examples are provided, in a nonlimiting sense to show specific skin barrier precursor compositions prepared and delivered in accordance with the present invention. Data relating to the performance characteristics of these compositions is also provided. In at least one instance an operable, but somewhat less than satisfactory comparative composition is set forth. Data with respect to the performance of exemplary compositions formulated will be found in Table I.

EXAMPLE 1

A film former composition was prepared by stirring 12 grams of n-butyl/iso-butyl methacrylate 50/50 copolymer into 85 grams of 95% isopropanol. After dissolution of the copolymer was complete, 3 grams of dimethyl phthalate was intimately blended into the solvated resin. The film former composition was then charged into a conventional container adapted for aerosol delivery of the contents by the use of a discharge assistant comprising isobutane. As seen in Table I, the performance of the composition when subjected to in vivo testing on human subjects is excellent with respect to the stated parameters considered highly desirable or necessary to the efficacy of a protective barrier film for the skin.

EXAMPLE 2

The procedure of Example 1 was repeated with the exception that the copolymer comprised 12.5 grams dissolved in 83.5 grams of isopropanol with the addition of 4 grams of DMP. The performance of this film former composition is set forth in Table I.

EXAMPLE 3

The procedure of Example 1 was repeated with the exception that the copolymer comprised 11.5 grams dissolved in 85.5 grams of isopropanol with the addition of 3 grams of DMP. The performance of this film former composition is set forth in Table I. This composition was further tested in vivo utilizing a dabbing applicator means in addition to aerosol applications.

EXAMPLE 4

The procedure of Example 1 was repeated with the exception that the copolymer comprised 11 grams dissolved in 86 grams of isopropanol with the addition of 3 grams of DMP. This formulation was tested in vivo using both the dabber and wipe applicator delivery systems and the performance is set forth in Table I.

EXAMPLE 5

The procedure of Example 1 was repeated with the exception that the copolymer comprised 10.5 grams dissolved in 86.5 grams isopropanol with the addition of 3 grams of DMP. This exemplary formulation was tested as stated in Example 4 and the results are set forth in Table I.

EXAMPLE 6

The procedure of Example 1 was repeated with the exception that the copolymer comprised 8 grams dissolved in 90 grams of 85% isopropanol with the addition of 2 grams of DMP. This formulation was tested in vivo utilizing the aerosol, dabber and wipe applicator delivery systems. As will be seen from the data in Table I, the performance of such formulation is somewhat less desirable than with the formulations of the prior examples.

EXAMPLE 7

The procedure of Example 1 was repeated with the exception that the copolymer comprised 5 grams dissolved in 93 grams of 95% isopropanol with the addition of 2 grams of DMP. From the test data as set forth in Table I, it will be appreciated that while this exemplary formulation is operable for the intended use, the performance is such that it is somewhat less than is normally desirable and necessary particularly when a person is standing during application.

It will be seen from the foregoing that the invention provides protective barrier film former composition as well as tailored delivery systems whereby ostomates and others are able to protect against, or significantly control, skin breakdown and the serious complications that oftentimes follow after skin breakdown.

I claim:

1. A film-former composition for application to the skin for providing a generally water insoluble, breathable skin barrier film for shielding peristomal skin, perineal skin and the like which comprises on the basis of weight from about 5% to about 12.5% of an acrylic resin selected from the group comprising butyl methacrylate, n-butyl/iso-butyl methacrylate copolymer dissolved in a physiologically acceptable relatively volatile solvent selected from $C_3$-$C_{10}$ alkanols and including a and minor proportion of a physiologically acceptable plasticizer.

2. The composition of claim 1 wherein the acrylic resin comprises n-butyl/iso-butyl methacrylate 50/50 copolymer.

3. The composition of claim 1 wherein the solvent is isopropanol.

4. The composition of claim 2 wherein the plasticizer is selected from the group comprising dimethyl phthalate and ethyl cellulose.

5. A film-former composition for aerosol application to the skin for providing a generally water insoluble breathable protective barrier film for shielding peristomal skin, perineal skin and the like which comprises on the basis of weight from about 10.5% to about 11.5% n-butyl/iso-butyl methacrylate 50/50 copolymer dissolved in a physiologically acceptable relatively volatile solvent selected from $C_3$-$C_{10}$ alkanols and plasticized with a minor amount of a physiologically acceptable plasticizer.

6. The composition of claim 5 wherein the solvent is isopropanol.

7. The composition of claim 5 wherein the isopropanol comprises about an 85% to about a 95% aqueous solution of isopropanol.

8. The composition of claim 5 wherein the plasticizer comprises dimethyl phthalate.

9. A film-former composition for wiping application to the skin for providing a generally insoluble breathable protective barrier film for shielding peristomal skin perineal skin and the like which comprises on the basis of weight from about 10.5% to about 11.5% n-butyl-/iso-butyl methacrylate 50/50 copolymer dissolved in a physiologically acceptable relatively volatile solvent selected from $C_3$-$C_{10}$ alkanols and plasticized with a minor amount of a physiologically acceptable plasticizer.

10. The composition of claim 9 wherein the solvent is isopropanol.

TABLE II

| PARAMETER | PERFORMANCE IN SPECIFIC WEIGHT CONCENTRATION OF COPOLYMER[1] | | | | | |
|---|---|---|---|---|---|---|
| | Examples 1&2 | Example 3 | Example 4 | Example 5 | Example 6 | Example 7 |
| Degree of Porosity of Breathability | E | G | VG | VG | G | P |
| Resistance to Penetration of Waste Materials | E | E | E | E | G | F-P |
| Adherence to Skin | E | E | E | E | G | F |
| Conformance to Skin Topography | E | E | E | E | E | G |
| Resistance to Fracture | E | E | E | E | VG | P |
| Resistance to Dissolution by Waste Materials and Water | E | E | E | E | E | E |
| Tendency to Resist Sag When Applied to Vertically Disposed Skin Surface | E | E | E | E | VG | F |

E = Excellent
VG = Very Good
G = Good
F = Fair
P = Poor

11. The composition of claim 5 wherein the isopropanol comprises about an 85% to about a 95% aqueous solution of isopropanol.

12. The composition of claim 5 wherein the plasticizer comprises dimethyl phthalate.

13. The article of claim 12 wherein the towelette comprises a textile having differential absorbability.

14. The article of claim 13 wherein the textile comprises a non-woven textile.

15. The article of claim 14 wherein the fibers comprising the non-woven textile are fusion bonded at discrete locations.

16. A film-former composition for application to the skin by means of a textile towelette for providing a generally water insoluble breathable skin barrier film for shielding peristomal skin, perineal skin and the like which comprises on the basis of weight from about 10.5% to about 11.5% n-butyl/iso-butyl methacrylate 50/50 copolymer dissolved in a physiologically acceptable relatively volatile solvent selected from $C_3$–$C_{10}$ alkanols and plasticized with a minor amount of a physiologically acceptable plasticizer.

17. The composition of claim 16 wherein the solvent is isopropanol.

18. A liquid film-former composition for application to the skin by means of gravometric feed of the liquid to a dabbing applicator for providing a generally water insoluble breathable skin barrier film for shielding peristomal, skin, perineal skin and the like which comprises on the basis of weight from about 11.5% to about 12.5% n-butyl/iso-butyl methacrylate 50/50 copolymer dissolved in a physiologically acceptable relatively volatile solvent selected from $C_3$–$C_{10}$ alkanols and plasticized with a minor amount of a physiologically acceptable plasticizer.

19. The composition of claim 18 wherein the solvent is isopropanol.

* * * * *